United States Patent [19]

Failla

[11] Patent Number: 4,976,722
[45] Date of Patent: Dec. 11, 1990

[54] SURGICAL HEMOSTATIC CLIPS

[75] Inventor: Stephen J. Failla, Chester, N.J.

[73] Assignee: Ethicon, Inc., Somerville, N.J.

[21] Appl. No.: 355,716

[22] Filed: May 22, 1989

[51] Int. Cl.⁵ .............................................. A61B 13/00
[52] U.S. Cl. ................................... 606/157; 606/151; 606/158
[58] Field of Search ....................... 606/151, 157, 158

[56] References Cited

U.S. PATENT DOCUMENTS

| | | | |
|---|---|---|---|
| 3,363,628 | 1/1968 | Wood | 606/158 |
| 3,867,944 | 2/1975 | Samuels | 606/158 |
| 3,874,042 | 4/1975 | Eddleman et al. | 606/157 |
| 4,146,130 | 3/1979 | Samuels et al. | 606/157 |
| 4,188,953 | 2/1980 | Klieman et al. | 606/157 |
| 4,346,869 | 8/1982 | MacNeill | 606/157 |
| 4,702,247 | 10/1987 | Blake, III et al. | 606/158 |
| 4,796,627 | 1/1989 | Tucker | 606/158 |
| 4,799,481 | 1/1989 | Transue et al. | 606/158 |
| 4,844,066 | 7/1989 | Stein | 606/158 |

Primary Examiner—Randall L. Green
Assistant Examiner—Gary Jackson
Attorney, Agent, or Firm—Paul A. Coletti; W. Brinton Yorks, Jr.

[57] ABSTRACT

A surgical hemostatic clip which afford substantially gapless closure includes a longitudinal groove formed in the tissue-contacting surface of one leg, and an opposing longitudinal tongue formed on the tissue-contacting surface of the other leg. In a preferred embodiment the longitudinal tongue and groove do not extend to the distal ends of the legs so as to provide distal flat surfaces on the tissue-contacting distal leg ends. Transverse grooves may be formed across the tongue and in intersection with the longitudinal groove to enhance the tissue-gripping characteristics of the hemostatic clip.

20 Claims, 3 Drawing Sheets

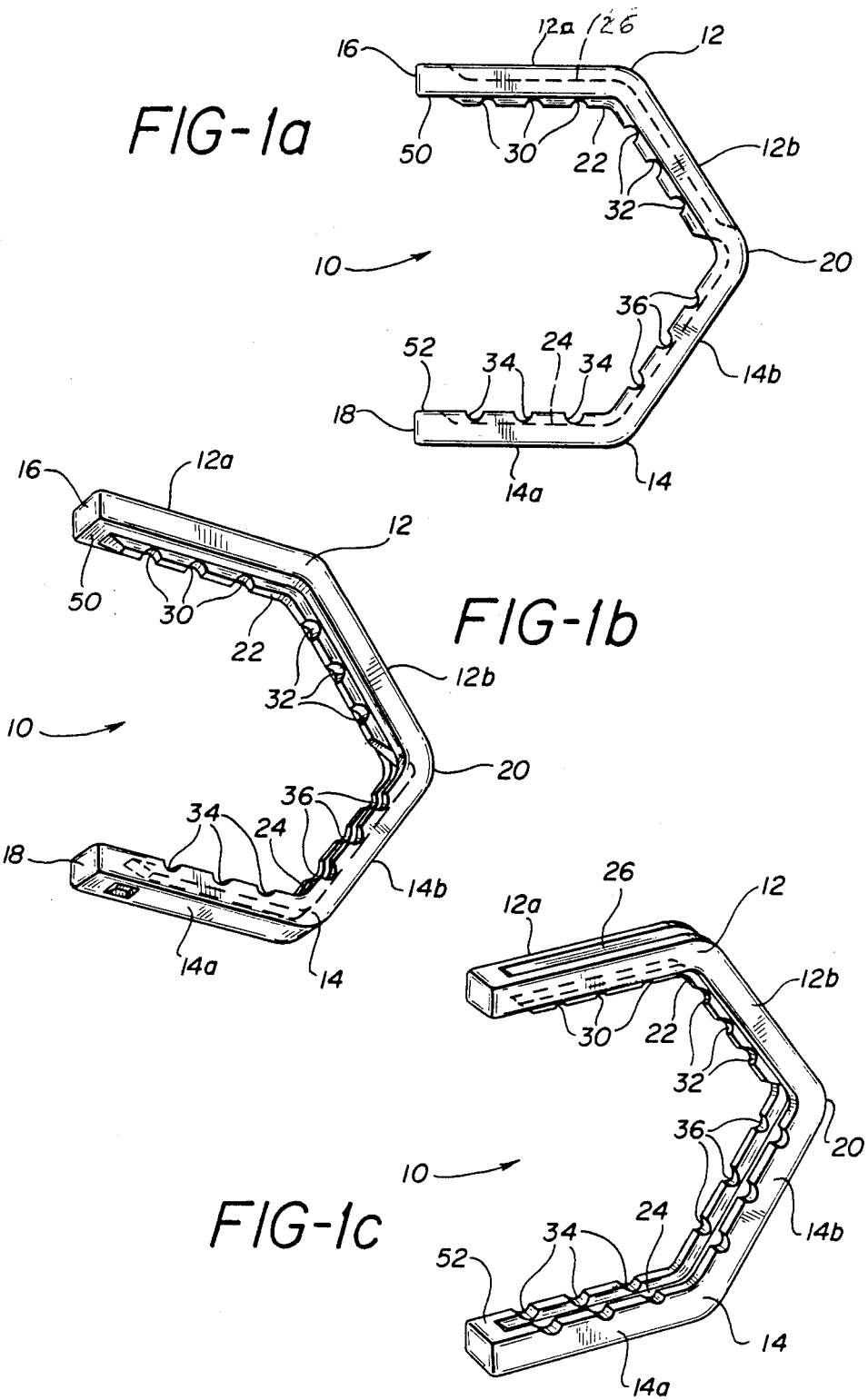

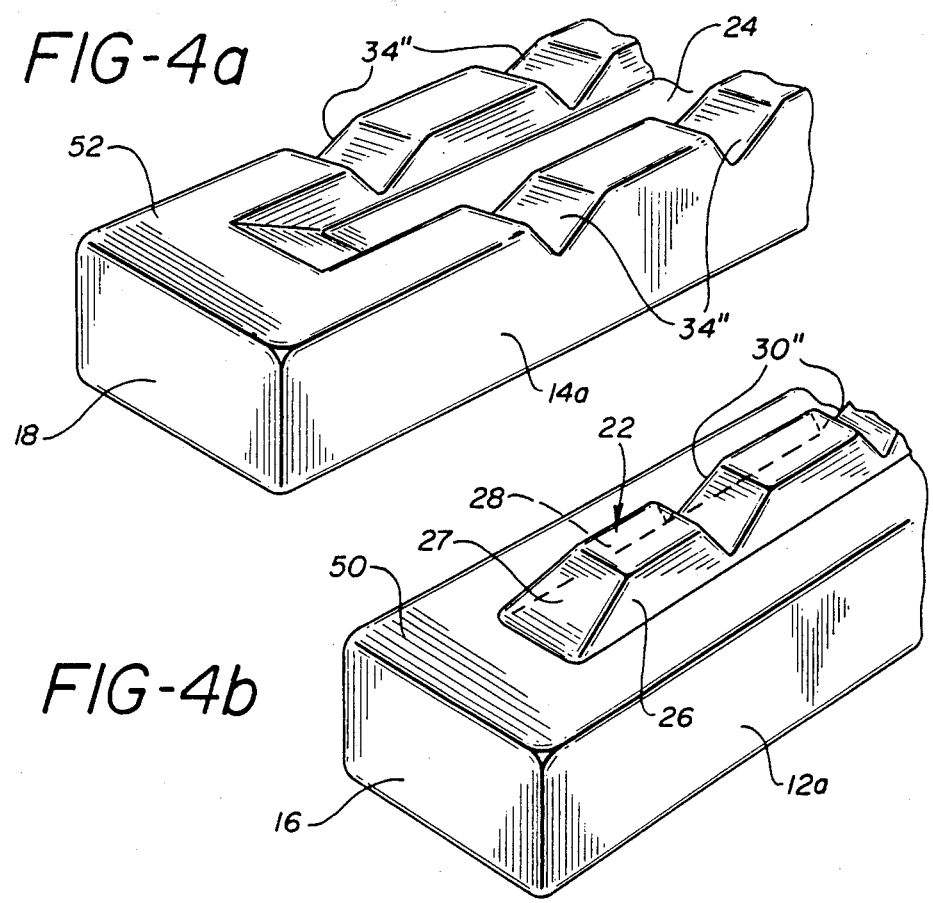
FIG-4a
FIG-4b
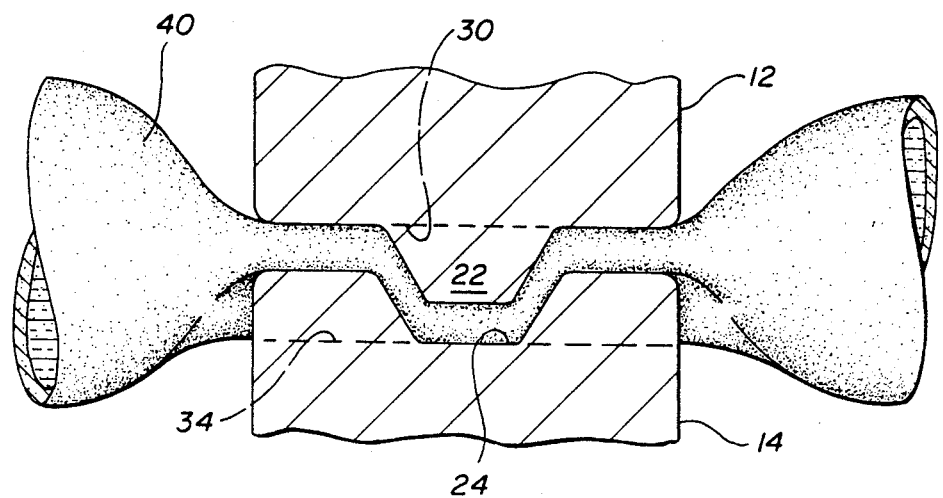
FIG-6

SURGICAL HEMOSTATIC CLIPS

This invention relates to devices used to close or shut tubular members and, more particularly, to metallic hemostatic clips used to close blood vessels within the body.

During many surgical procedures, the surgeon will have to close or ligate various blood vessels before severing the vessels in order to prevent excessive bleeding and reduce the risk to the patient of blood loss. One technique to close a blood vessel is to ligate it; that is, tie a surgical suture about the vessel to close the vessel. Also, there are various types of metal devices or clips having a pair of legs connected at their proximal ends that can be placed about the vessel and the legs urged or squeezed together to shut the blood vessel. Hemostatic clips are well known in the prior art and are disclosed in numerous U.S. patents as, for example, U.S. Pat. Nos. 3,439,523; 3,270,745; 3,363,628; 3,463,156; 3,439,522; 3,439,523; 4,146,130; and 4,449,530.

It is desirable for a hemostatic clip to have strong retentive properties when clamped about or hemastosizing a blood vessel. In a typical surgical procedure, it is necessary for a surgeon to hemastosize and then sever numerous blood vessels before attending to the purpose of the particular procedure. Thus, a surgeon will hemastosize and sever blood vessels, then direct his attention to performing the necessary surgery, forgetting about the hemastosized vessels. However, the danger of bleeding can arise if the. Sturgeon should brush against the clipped vessels, or wipe them with a sponge, while concentrating on other activities. Should the clips snag or become caught on a sponge or other article, it is possible for insecurely applied hemostatic clips to slide axially off the end of a severed vessel, leading to unnecessary bleeding. Accordingly, it is desirable for a clip to be securely attached to a vessel to obviate the problem of accidental dislodgment.

Not only should a hemostatic clip securely hemastosize a blood vessel, but it must also be reliably capable of application without "scissoring." Scissoring refers to the failure of the legs of the clip to align with one another as the clip is closed by the clip applicator. Should the legs fail to align, both the hemostatic and retentive capabilities of the hemostatic clip are compromised.

A hemostatic clip which is directed toward meeting these needs is described in U.S. Pat. No. 4,799,481. The hemostatic clip therein described includes two legs which are proximally joined at a hinge region. A longitudinal groove is formed in the tissue-contacting surface of each leg, and the longitudinal grooves are intersected by a number of angled transverse grooves. The longitudinal grooves do not extend fully to the distal ends of the legs, but leave distal flat surfaces at the ends of the legs. When the clip is closed, tissue will fill in the grooves and be tightly compressed by the legs outside the grooves, providing secure retention on the vessel. The distal flat ends of the legs provide surfaces which will contact each other initially as the clip is closed. The contact of the distal flat surfaces will cause the legs to straighten in alignment with each other, thereby minimizing the possibility of scissoring.

It would be desirable to provide even more secure, positive hemostasis than that provided by the hemostatic clips of the prior art. Not only must the hemostasis provided by the clips be reliable, but positive retentive forces should develop to minimize the possibility of clips sliding off of a blood vessel. In addition, the possibility of scissoring upon closure should also be minimized.

In accordance with the principles of the present invention, hemostatic clips are described which provide secure, positive hemostasis of a blood vessel. Each clip includes two legs which are joined at their proximal ends by a hinge region. A longitudinal groove is formed in the tissue-contacting surface of one of the legs. A mating longitudinal projection extends from the opposing leg. When the clip is closed, the longitudinal projection aligns with the longitudinal groove in a tongue in groove type of alignment, providing positive gripping of the hemastosized vessel. While the longitudinal groove and projection may extend fully to the distal ends of the legs, in a preferred embodiment the longitudinal groove and projection do not extend fully to the distal ends of the legs, leaving distal flat surfaces at the end of each leg. Upon closure these distal flat surfaces will contact initially, promoting aligned closure of the legs without scissoring. As the clip is further closed the distal end of the projection engages the groove and performs a secondary alignment function.

In a preferred embodiment of the present invention a plurality of transverse grooves intersect the longitudinal groove, and a plurality of angled transverse grooves intersect the longitudinal projection. Even more secure attachment will result during closure as tissue fills in these opposing grooves of the hemostatic clip legs.

In the drawings:

FIGS. 1a, 1b, and 1c illustrate various views of a hemostatic clip constructed in accordance with the principles of the present invention:

FIGS. 2a, 2b, and 2c are cross-sectional views of various tongue and groove geometries;

FIGS. 4a and 4b are elevational views of the distal ends of a hemostatic clip of the present invention;

FIG. 6 is a partially cross-sectional view of a hemostatic clip of the present invention when hemastosizing a blood vessel.

Figure 2C:
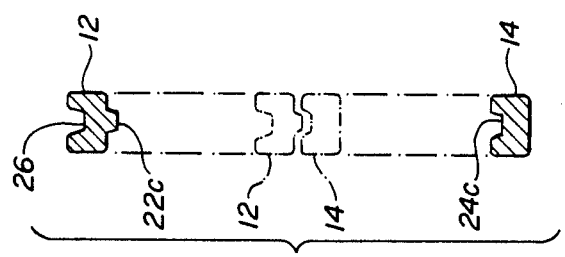

Referring to FIGS. 1a, 1b, and 1c, a hemostatic clip 10 constructed in accordance with the principles of the present invention is shown. The clip 10 may be made of any of the conventional variety of surgical metals which can be sterilized and are nontoxic and can therefore be tolerated within the body for indefinite periods of time. Suitable materials with these characteristics include stainless steel, titanium, and tantalum. The clip may be conveniently formed from wire of these materials into the "barn" shape illustrated in the FIGURES. When produced in the angular shape shown in the drawings, a number of such clips may be conveniently stored prior to use in a cartridge as described in U.S. Pat. No. 4,799,481.

The clip 10 comprises two legs 12 and 14, which are joined at their proximal ends by a hinge 20. The legs also have distal ends 16 and 18. Each leg is divided into a proximal section 12b, 14b and a distal section 12a, 14a by a "knee" bend intermediate the proximal and distal ends of each leg.

Projecting outward from the tissue contacting surface of the leg 12 is a longitudinal projection or tongue 22. The tongue extends from a proximal point near the hinge 20 to a point near the distal end of the leg 12. The tongue 22 terminates short of the distal end 16 so as to leave a distal flat surface 50 on the tissue contacting surface of leg 12. Formed in leg 14 is a complementary groove 24. The groove 24 begins at the end of the tongue 22 on leg section 12b and extends along leg 14 to a point near the distal end of the leg, leaving a distal flat surface 52 on the tissue contacting end of leg section 14a. The thickness of the leg 14 containing the groove is preferably slightly greater than the thickness of the leg 12 containing the tongue to permit the formation of a groove deeper than the height of the tongue and also to equalize the section moduli.

Intersecting the groove 24 along the leg 14 are a plurality of angled transverse grooves 36 and 34, which intersect the groove 24 at different angles. The grooves 36 intersect the central longitudinal groove 24 along the proximal leg section 14b at an angle of approximately 60°. The grooves 34 intersect the groove 24 along the distal leg section 14a at an angle of approximately 60° in a reverse sense. Intersecting the tongue 22 along the leg 12 are a plurality of angled transverse grooves 30 and 32, which grooves intersect the tongue normal to the longitudinal axis of the leg 12. In the embodiment of FIGS. 1a, 1b, and 1c the transverse grooves 30, 32, 34, and 36 have a curvilinear concave form.

Figure 2B:
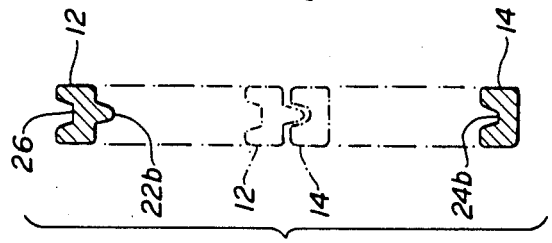
Figure 2A:
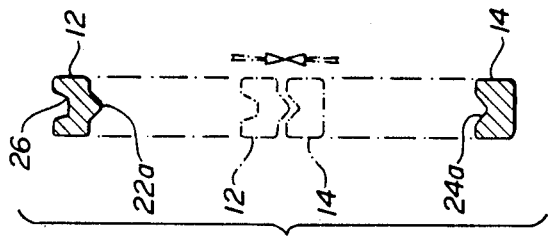

FIGS. 2a, 2b, and 2c are cross-sectional illustrations of tongue and groove combinations with different geometrical shapes. FIG. 2a shows leg 12 with a triangular V-shaped tongue 22a. The apex of the V-shaped tongue 22a may be relatively pointed or is preferably slightly rounded to avoid unnecessary trauma to the hemastosized blood vessel. The applier contacting surface of the leg 12 is shown to have a groove 26, which is a result of the coining of the leg employed to form the tongue 22a. FIG. 2a also shows the leg 14 with a complementary V-shaped groove 24a. Shown in the center of FIG. 2a in phantom are mated legs 12 and 14 with the V-shaped tongue and groove geometry.

FIG. 2b illustrates leg 12 with a rounded, bell-shaped tongue 22b. The tongue 22b mates with the bell-shaped groove 24b of the leg 14. The mating of the two legs with this tongue and groove geometry is shown in phantom in the center of FIG. 2b. In a similar fashion FIG. 2c illustrates a preferred geometry for the tongue and groove combination, which is a rectilinear, box-like shape. The projecting tongue 22c is seen to exhibit a trapezoidal cross-sectional shape, as does the groove 24c. Shown in phantom in the center of FIG. 2c is the mating of the trapezoidal tongue 22c and groove 24c.

Figure 3:
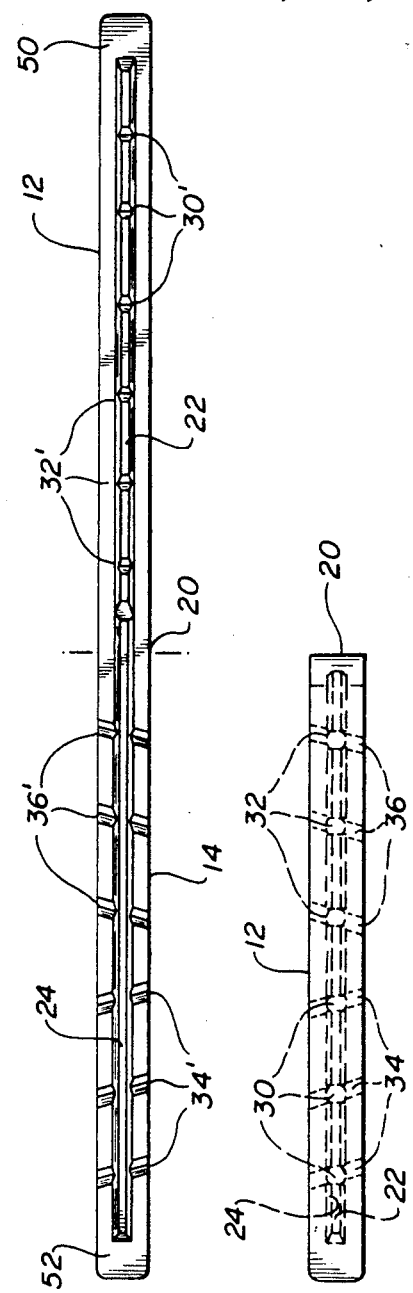
FIG. 3 is a plan view of the inner, vessel contacting surface of a hemostatic clip of the present invention in a flat, open condition.

FIG. 3 is a plan view of the tissue-contacting surface of a preferred hemostatic clip of the present invention when the clip is straightened to a flat, open condition. The clip is seen to have distal flat surfaces 50 and 52 at the two distal ends of the clip. The longitudinal center groove 24 of leg 14 is seen to have V-shaped transverse grooves 34' intersecting a trapezoidal longitudinal groove 24 toward the distal end. Intermediate the distal section and the hinge region 20 the longitudinal groove is intersected by V-shaped transverse grooves 36' at a second angular orientation with respect to the first set of transverse grooves. To the right of the hinge region the groove 24 undergoes a transition to a trapezoidal tongue 22 on the leg 12. The tongue 22 extends to the distal flat surface 50 and is intersected by normally directed V-shaped grooves 30', 32'. The distal flat surface 50 at the end of the tongue 22 is longer than the distal flat surface 52 at the end of the groove to insure that upon closure the tongue 22 will not extend beyond the distal end of the groove 24 and prevent complete distal closure of the clip.

The distal ends of a further embodiment of a hemostatic clip of the present invention are seen in enlarged elevational views in FIGS. 4a and 4b. The distal end of the leg 14, shown in FIG. 4a, exhibits V-shaped transverse grooves 34''. Unlike the symmetrical V-shaped transverse grooves of the embodiment of FIG. 3, the V-shaped grooves of FIGS. 4a and 4b are canted with the distal wall of each groove being more normally oriented and the proximal wall being more acutely oriented. These canted grooves will provide greater resistance to lateral slippage of a blood vessel clamped between the legs of the clip. The transverse grooves 34'' intersect the trapezoidal longitudinal groove 24, which is seen to have angled side walls designed to mate with a trapezoidal tongue. It is also seen that the transverse grooves do not extend to the full depth of the longitudinal groove 24. In FIG. 4b the trapezoidal tongue 22 is seen with its angled side walls 26 and 28, and an angled end wall 27, thereby providing the trapezoidal cross-sectional shape. A preferred shape is to have the flat top of the trapezoid be approximately one-third the width of the base of the trapezoid. In the embodiment of FIG. 4b, like FIG. 4a, the transverse grooves 30'' are formed as distally canted V-shaped grooves which do not extend to the full depth of the tongue 22.

In use the hemostatic clips of the present invention are packaged in a clip cartridge as shown in U.S. Pat. No. 4,799,481. A clip is removed from the cartridge by grasping the outer, applier contacting surface of the legs between the slotted tips of an applier instrument as shown in that patent. The clip is removed from the cartridge and then held in the applier instrument in its characteristic "barn" shape. The open clip is placed around a blood vessel which is to be hemastosized, with the vessel generally centered between the clip legs. As the applier instrument is actuated to close the clip, the distal ends of the clip will approach each other and meet, with the vessel now completely encircled by the clip. Because the distal ends 50, 52 of the clip are flat, they will contact each other without causing any lateral movement of the legs with respect to each other, movement which could cause the legs to misalign and scissor. As further compression is applied to the instrument, the knee bends will straighten and the hinge will close until the two legs 12 and 14 are straightened against each other with the blood vessel hemastosized between them. A hemastosized blood vessel is illustratively shown between the legs of the clip in FIG. 6.

Figure 5:
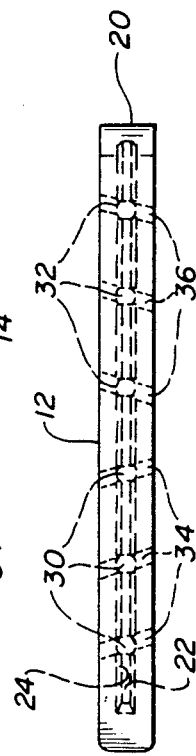
FIG. 5 is a plan view of the hemostatic clip of FIG. 3 in a closed condition.

The hemostatic clips of the present invention will remain securely fastened around a blood vessel and will resist forces which could cause a more traditional hemostatic clip to slide along the vessel and off of the end of a severed vessel. Primarily this capability is provided by the mating tongue and groove, whereby the vessel is forced into the groove 24 by compression from the tongue 22. This leaves the vessel clamped in the undulating configuration as shown in FIG. 6. As opposed to a traditional clip which compresses the vessel in a linear path between the legs of the clip, the undulation provided by the tongue and groove is a substantial deterrent to forces which would tend to slide the clip along the vessel. Additionally the pattern of the transverse grooves distributes varying compressive forces in line with, across, and at different angles relative to the axis of the vessel. This can be appreciated from the plan view of the closed hemostatic clip of FIG. 5, which shows in phantom the different angular intersections of the tongue 22 and longitudinal groove 24, the differently angled transverse grooves 34 and 36, and the normally transverse grooves 32 of the tongue 22. The filling of these differently oriented grooves by vessel tissue further aids in the retentive capability of the hemostatic clips of the present invention.

Furthermore, the tongue and groove hemostatic clips of the present invention require no specialized hinge structure to assist in clip closure and prevent gapping in the hinge region. U.S. Pat. No. 4,449,530 for example teaches the use of a box-like hinge structure, and U.S. Pat. No. 4,799,481 teaches the use of a V-shaped notch at the hinge region. While affording substantially gapless closure at the hinge region, these hinge techniques act to reduce the modulus of the metal at the hinge regions. The hemostatic clips of the present invention require no reduction in the modulus at the hinge but still afford gapless closure due to the tongue and groove configuration. By locating the transition from tongue to groove on the tongue side of the hinge 20 but in close proximity thereto as shown in the drawings, the tongue 22 will engage the groove 24 near the hinge as the clip is closed. Thus, even if the lateral surfaces of the clip do not fully meet when the clip is closed, a gapless closure is provided by the engagement of the tongue 22 and the groove 24. The undiminished modulus of the hinge 20 provides a strong hinge which will keep the clip securely clamped about the hemastosized blood vessel. Moreover, this hinge configuration provides an even greater modulus than a hinge with a simple rectangular cross-section of the same area and width due to the greater thickness of the clip at the hinge region.

What is claimed is:

1. A hemostatic clip comprising first and second legs each leg having a tissue contacting surface and an applier contacting surface and each leg having a distal end and joined at their proximal ends in a hinge region, said first leg including a longitudinal projection extending along at least a substantial length of said first leg for engaging a longitudinal groove formed in said second leg and extending along at least a substantial length of said second leg, whereby engagement of said longitudinal projection and said longitudinal groove affords substantially gapless closure of said clip, and wherein said longitudinal groove and said longitudinal projection are formed on the tissue contacting surface of said legs, said applier contacting surfaces of said legs formed wherein the dimension between the applier contacting surface and tissue contacting surface of said second leg is greater than the dimension between the applier contacting surface and tissue contacting surface of said first leg.

2. The hemostatic clip of claim 1, further comprising a plurality of transverse grooves extending across said longitudinal projection.

3. The hemostatic clip of claim 2, wherein said transverse grooves are directed substantially normal to the longitudinal axis of said first leg.

4. The hemostatic clip of claim 1, further comprising a plurality of transverse grooves extending across said second leg on either side of said longitudinal groove.

5. The hemostatic clip of claim 4, wherein said transverse grooves intersect said longitudinal groove at an acute angle.

6. The hemostatic clip of claim 5, wherein ones of said transverse grooves intersect said longitudinal groove at a first angle in a given direction, and others of said transverse grooves intersect said longitudinal groove at a second angle in said given direction.

7. The hemostatic clip of claim 4, wherein the depth of ones of said transverse grooves is less than the depth of said longitudinal groove.

8. The hemostatic clip of claim 1, wherein each of said longitudinal projection and groove terminates prior to the distal end of each respective leg, and further comprising distal flat surfaces formed between the termination of said projection and groove and the distal end of each of said legs.

9. The hemostatic clip of claim 8, wherein the longitudinal length of said distal flat surface of said first leg is greater than the longitudinal length of said distal flat surface of said second leg.

10. The hemostatic clip of claim 1, wherein said longitudinal projection and said longitudinal groove make a transition from one to the other on said first leg near said hinge region.

11. The hemostatic clip of claim 1, wherein each of said longitudinal projection and said longitudinal groove are generally V-shaped in cross-section.

12. The hemostatic clip of claim 1, wherein each of said longitudinal projection and said longitudinal groove are generally bell-shaped in cross-section.

13. The hemostatic clip of claim 1, wherein each of said longitudinal projection and said longitudinal groove are generally rectilinear in cross-section.

14. The hemostatic clip of claim 13, wherein each of said longitudinal projection and said longitudinal groove are generally trapezoidal in cross-section.

15. The hemostatic clip of claim 1 wherein said applier contacting surface of said first leg contains a groove engageable with an applier for clamping said first leg on said second leg.

16. The hemostatic clip of claim 2 or 4, wherein said transverse grooves are V-shaped.

17. The hemostatic clip of claim 8, wherein said V-shaped grooves are canted with the distally oriented wall directed more normally with respect to the longitudinal axis of its clip leg and the proximally oriented wall directed more acutely with respect to the longitudinal axis of its clip leg.

18. The hemostatic clip of claim 2 or 4, wherein said transverse grooves are concave curvilinear shaped.

19. The hemostatic clip of claim 2 or 4, wherein said transverse grooves are trapezoid shaped.

20. The hemostatic clip of claim 2, wherein the depth of ones of said transverse grooves is less than the height of said longitudinal projection.

* * * * *